United States Patent [19]

Robert et al.

[11] Patent Number: 4,567,888
[45] Date of Patent: Feb. 4, 1986

[54] DEVICE FOR TREATING RESPIRATORY DEFICIENCY OF A PATIENT

[75] Inventors: Dominique Robert, Champagne-Au-Mont D'Or; François Perrin, La Mulatiere; Gilles Bally, Lyons, all of France

[73] Assignee: Compagnie Francaise de Produits Oxygenes, Paris, France

[21] Appl. No.: 507,467

[22] Filed: Jun. 24, 1983

[30] Foreign Application Priority Data

Jul. 13, 1982 [FR] France ............................ 82 12264

[51] Int. Cl.$^4$ ........................................... A61M 16/00
[52] U.S. Cl. ........................... 128/204.21; 128/204.23; 128/207.18; 128/724; 128/204.24
[58] Field of Search ............... 128/716, 719, 724, 736, 128/204.18, 204.19, 204.21, 204.23, 205.24, 671, 204.26; 340/825.59, 870.16, 870.17; 73/198, 109, 203, 204, 861.44

[56] References Cited

U.S. PATENT DOCUMENTS

| 3,191,595 | 6/1965 | Wilson | 128/204.23 |
| 3,232,288 | 2/1966 | Krobath | 128/724 |
| 3,316,902 | 5/1967 | Winchel et al. | 128/204.23 |
| 3,802,417 | 4/1974 | Lang | 128/724 |
| 3,831,596 | 8/1974 | Cavallo | 128/204.23 |
| 3,903,875 | 9/1975 | Hughes | 128/724 |
| 3,952,739 | 4/1976 | Cibulka | 128/204.23 |
| 3,972,327 | 8/1976 | Ernst et al. | 128/204.21 |
| 4,256,101 | 3/1981 | Ellestad | 128/204.23 |
| 4,336,590 | 6/1982 | Jacq et al. | 128/204.23 |
| 4,357,936 | 11/1982 | Ellestad et al. | 128/204.23 |
| 4,420,001 | 12/1983 | Hearne | 128/724 |
| 4,457,303 | 7/1984 | Durkan | 128/207.18 |
| 4,465,067 | 8/1984 | Koch et al. | 128/207.18 |

FOREIGN PATENT DOCUMENTS

| 2809255 | 9/1978 | Fed. Rep. of Germany . | |
| 2125449 | 9/1972 | France . | |
| 2309207 | 11/1976 | France . | |
| 2346025 | 10/1977 | France . | |
| 197712 | 12/1977 | U.S.S.R. | 128/724 |

Primary Examiner—Henry J. Recla
Assistant Examiner—Karin M. Reichle
Attorney, Agent, or Firm—Young & Thompson

[57] ABSTRACT

A duct opening close to the patient's respiratory passages provides a supply of additional oxygen from a source.

The device comprises a heat sensor element exposed to the temperature changes between the air inhaled and the air exhaled which cause corresponding voltage changes across its terminals; a coupler supplying signals which are a function of these voltage changes; an electromagnetic valve in the duct and controlled by a control element during the patient's various stages of respiration.

The invention is applicable more particularly to oxygen therapy devices worn on the person e.g. in the fashion of spectacles.

7 Claims, 3 Drawing Figures

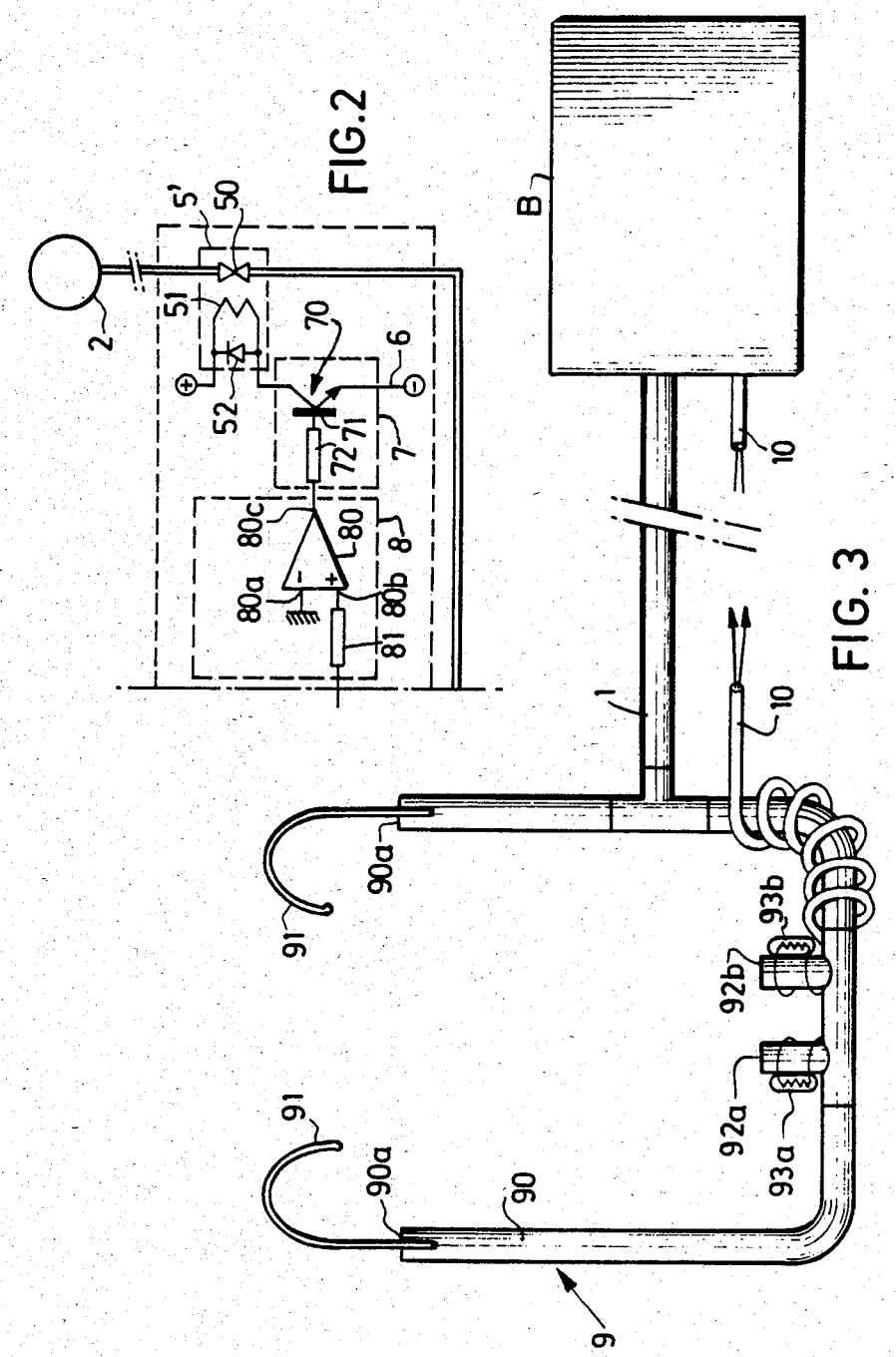

DEVICE FOR TREATING RESPIRATORY DEFICIENCY OF A PATIENT

BACKGROUND OF THE INVENTION

The present invention relates to a device for treating respiratory deficiency of a patient by additional supply of oxygen fed from a source through at least one duct the end of which opens close to the respiratory passages of the patient to supplement the supply of oxygen inhaled from the surrounding air by the patient.

A variety of devices of this kind are available, and provide the patient with an oxygen enrichment of the air normally breathed in by existing respiratory passages, essentially being the nostrils or else the mouth. One of the most widely applied devices is the oxygen breathing mask which can be fitted to the face and comprises two protrusions allowing oxygen to be supplied to both nostrils of the patient.

However, the devices known until now are fitted with a simple manual valve commonly inserted into the aforesaid duct which is opened by the patient when the apparatus is put in operation. This system has the disadvantage however that the oxygen is fed continuously whereas its supply is useful only during the inhalation stages and represents a total loss during the exhalation stages.

This loss, which is costly per se, represents an even more substantial disadvantage in the case of portable sets for which the capacity of the oxygen source determines the radius of action.

It is an object of the invention to eliminate or minimise the aforesaid shortcomings.

SUMMARY OF THE INVENTION

To achieve this and other objects, the device according to the invention comprises at least one thermistor located adjacent said duct end and connected in a temperature detector circuit in series with a voltage source and a resistor in such manner that the temperature changes between the air inhaled and the air exhaled cause corresponding voltage changes across the terminals of the said thermistor, a coupler connected to said thermistor being provided to deliver electric signals as a function of said voltage changes, an electromagnetic valve connected in aforesaid duct and connected to an electric supply circuit and a control element for said supply circuit energised by said coupler and controlling said electromagnetic valve during the patient's various stages of respiration.

Due to the heat sensor element, the device in accordance with the invention consequently renders it possible to detect the inhalatory stages and exhalatory stages and to exert a corresponding control over the opening or closing of the electromagnetic valve, and consequently over the supply of oxygen. The adjustment of the components of the device is such that the electromagnetic valve is open during the inhalatory stages and closed during the exhalatory stages, thus ensuring that the oxygen is supplied only at the required times.

The resultant saving of oxygen not only entails a saving in cost since it renders it possible to delay recharging the bottles, but also allows appreciably greater autonomy than with conventional apparatuses, in the case of portable apparatuses.

According to another feature of the invention, the control element causes the opening of the electromagnetic valve, which is closed in the absence of voltage, during the inhalatory stages.

According to another feature of the invention, the control element causes the closing of the electromagnetic valve, which is open in the absence of voltage, during the exhalatory stages.

According to yet another feature of the invention applied to an oxygen breathing mask in which the aforesaid oxygen duct has two protrusions intended for insertion into the patient's nostrils, the heat sensor element comprises two thermistors inserted in parallel into the electric current supply circuit and the said thermistors being located adjacent the aforesaid protrusions.

BRIEF DESCRIPTION OF THE DRAWINGS

In order that the invention may be more clearly understood, reference will now be made to the accompanying drawings which show certain embodiments thereof by way of example and in which:

FIG. 2 is a partial view of the layout of FIG. 1 showing a modified embodiment of the invention, FIG. 3 illustrates an oxygen breathing mask fitted with the device in accordance with the invention.

DETAILED DESCRIPTION OF THE PREFERRED EMBODIMENTS

Figure 1:
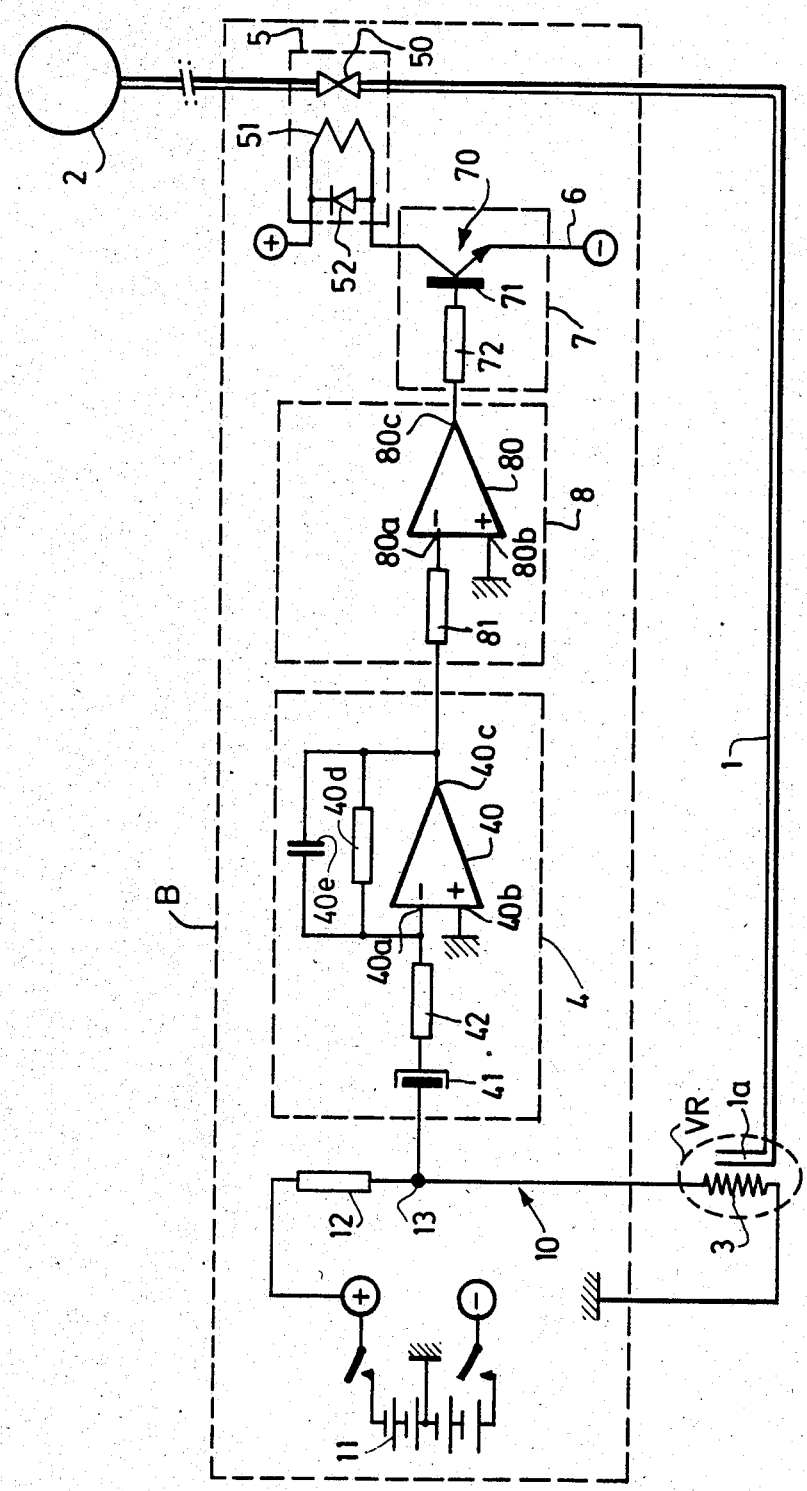
FIG. 1 illustrates the layout of a device in accordance with the invention.

Referring now the drawings and firstly to FIG. 1, a duct 1 is connected to a source 2 of "top-up" oxygen under pressure and has an open end 1a opening in direct proximity to the respiratory passages of the patient denoted diagrammatically at VR.

A heat sensor element formed by a thermistor 3 is also placed in direct proximity to the respiratory passages VR and to the end 1a of the duct 1. This thermistor 3 is connected in a circuit 10 for detection of temperature changes, comprising a voltage source 11 and a resistor 12 in series with the thermistor 3. This resistor and this thermistor each have one of their terminals connected to a common point 13.

The changes in temperature between the air inhaled and the air exhaled by the patient cause corresponding changes in the value of the resistivity of the thermistor 3 whereas the resistor is unaffected by these temperature changes. Voltage changes corresponding to these temperature changes consequently appear across the terminals of the thermistor, and therefore a voltage signal appears between the terminal 13 and ground.

The device also comprises a coupler 4 which receives the aforesaid voltage signals and delivers the corresponding output signals, an electromagnetic valve 5 which is normally closed in the absence of voltage and fitted in the duct 1, an electric supply circuit 6 for the said electromagnetic valve, and a control element 7 for the supply circuit, this element 7 receiving signals from the coupler 4 via a shaping element 8. The whole of the circuit 10, (except for the thermistor), the coupler 4, the electromagnetic valve 5, the circuit 6, the element 7 and the shaping element 8, are installed in a housing shown at B.

The coupler 4 comprises an amplifier 40 one of the terminals 40a of which is connected via a coupling capacitor 41 and an input resistor 42, and in parallel with a resistor 40d and a capacitor 40e, to the terminal 13 of the circuit 10, whereas its other input terminal 40b is connected to ground.

The electromagnetic valve 5 comprises an element 50 for opening and closing the duct 1 and a winding 51 connected in the supply circuit 6. A diode 52 provides protection for the transistor 70.

The control element 7 of the supply circuit 6 essentially comprises a transistor 70 having a base 71 and provided with an input resistor 72. This base 71 being polarised by the signals appearing at the output terminal 40c of the amplifier 40 which are then fed to the resistor 72 via the shaping element 8. This latter essentially comprises an amplifier 80 of which one of the terminals 80a (negative) is connected to the terminals 40c via an input resistor 81, its other input terminal 80b (positive) is grounded whereas its output terminal 80c is connected directly to the resistor 72.

In step with the inhalatory and exhalatory stages of the patient, the thermistor 3 is exposed to temperature changes causing a variable voltage signal to appear at the terminal 13. This signal is amplified and derived by the coupler 4 and is consequently converted into a positive or negative signal which is fed to the base 71 of the transistor via the shaping element 8. During the inhalatory stage, the output signal of the shaping element 8 is positive and operates the opening of the electromagnetic valve, whereas during the exhalatory stage, it is negative and operates its closure.

In the modified embodiment illustrated in FIG. 2, in which the same reference numbers denote the same elements as in FIG. 1, the resistor 81 is connected to the positive terminal 80b of the amplifier 80, the negative terminal 80a of which is grounded. Furthermore, the electromagnetic valve 5' installed in the circuit 1 is normally open in the absence of voltage.

During the inhalatory stage, the output signal of the shaping element 8 is negative and operates or maintains the opening of the electromagnetic valve 5', whereas it is positive during the exhalatory stage and operates its closing. This layout has the advantage in case of a breakdown of the electric supply system or of an element of the electronic system, of allowing the arrival of oxygen at the patient's respiratory passages.

An application of the invention to an oxygen breathing mask has been illustrated in FIG. 3, in which the same reference numbers denote the same elements as in FIGS. 1 and 2. The mask generally denoted by 9, is formed by a pipe 90 closed at its ends 90a and substantially assuming the shape of the face in such manner that it may be worn by a patient in the fashion of spectacles. Branches 91 at the extremities of the pipe 90 render it possible to secure the "spectacles" over the ears. The pipe 90 includes two protrusions 92a and 92b the ends of which are open and which open in the patient's nostrils when the "spectacles" are in position on the face, who consequently receives the "top-up" oxygen supplied via the duct 1. On each of the protrusions 92a and 92b is provided a thermistory 93a and 93b, these two thermistors being arranged in parallel and connected in the circuit 10 for detection of temperature changes (see FIG. 1). The fact that two thermistors are provided in parallel renders it possible to increase the reliability of the apparatus, by allowing the latter to continue to work even in case of breakdown of one of the thermistors.

The invention is not restricted in any way to the embodiments described and illustrated, which were given by way of non-limiting examples.

We claim:

1. A device for treating respiratory deficiency of a patient by the supply of oxygen from a source of oxygen to supplement a supply of oxygen inhaled from the surrounding atmosphere by the patient, comprising a duct having two open ends, means for connecting one end of said duct to the source of oxygen, protrusion means at the other open end of said duct adapted to be inserted into each of the patient's nostrils for delivering oxygen thereto from said duct which protrusion means includes thermistor means capable of detecting a change in temperature of air passing through the patient's nostrils, means to retain said protrusion means within the patient's nostrils, valve means in said duct adapted to control the flow of oxygen through the said duct from said source of oxygen, means responsive both to a decrease in temperature detected at the beginning of the patient's inhalation by said thermistor means as a result of the flow of air into said nostrils upon inhalation and to a temperature increase detected at the beginning of the patient's exhalation by said thermistor means as a result of the flow of air from said nostrils upon exhalation, said means responsive to said temperature decrease or temperature increase adapted to cause said valve means to be open upon detection of a decrease in temperature by said thermistor means and to cause said valve means to be closed upon detected of an increase in temperature by said thermistor means, whereby the period of time that the valve means is open is coextensive with the patient's inhalation and the period of time that the valve means is closed is coextensive with the patient's exhalation.

2. A device as claimed in claim 1, wherein said means responsive to said increase or decrease in temperature comprises a temperature detector circuit in which said thermistor means is connected in series with a voltage source and a resistor such that the change in temperature of the air passing through the patient's nostrils causes corresponding voltage increases or decreases across the thermistor means, and a coupler means connected to said thermistor means for delivering electric signals as a function of said voltage increases or decreases, said valve means being an electromagnetic valve means which is connected to an electric supply circuit, and control means for said supply circuit which control means is energized by said coupler means as a result of said electric signals to control the position of said electromagnetic valve means during inhalation and exhalation.

3. A device as claimed in claim 2, in which said coupler means comprises an amplifier which has an input terminal that receives said increasing or decreasing voltage from said thermistor means and an output terminal that delivers electrical signals the polarity of which is a function of whether the voltage is increasing or decreasing.

4. A device as claimed in claim 3, in which a transistor in said electric supply circuit of said electromagnetic valve defines said control means, said transistor having a base, a shaping means connected to said base and the output terminal of said amplifier such that said transistor base is supplied with said electrical signal from the output terminal of said amplifier via said shaping means.

5. A device as claimed in claim 1, in which said valve means is normally closed.

6. A device as claimed in claim 1, in which said valve means is normally open.

7. A device as claimed in claim 1, said thermistor means comprising two thermistors connected in parallel, one said thermistor adapted to be inserted into each of the patient's nostrils, respectively, and being carried by said protrusion means therein.

* * * * *